(12) United States Patent
Ichikawa

(10) Patent No.: US 9,333,072 B2
(45) Date of Patent: May 10, 2016

(54) INTRAOCULAR LENS

(71) Applicant: CHUKYO MEDICAL CO., INC., Nagoya-shi, Aichi (JP)

(72) Inventor: Kazuo Ichikawa, Nagoya (JP)

(73) Assignee: CHUKYO MEDICAL CO., INC., Nagoya-Shi, Aichi (JP)

( * ) Notice: Subject to any disclaimer, the term of this patent is extended or adjusted under 35 U.S.C. 154(b) by 35 days.

(21) Appl. No.: 14/264,371

(22) Filed: Apr. 29, 2014

(65) Prior Publication Data

US 2015/0305858 A1    Oct. 29, 2015

(51) Int. Cl.
*A61F 2/16*    (2006.01)

(52) U.S. Cl.
CPC ........... *A61F 2/16* (2013.01); *A61F 2002/1681* (2013.01); *A61F 2002/1683* (2013.01); *A61F 2002/1689* (2013.01)

(58) Field of Classification Search
CPC .. A61F 2/16–2002/169053; A61F 2250/0008; A61F 2250/0065; A61F 2250/0091; A61F 2220/0008–2220/0016
USPC ............... 623/6.42, 6.51–6.54, 6.34, 6.32
See application file for complete search history.

(56) References Cited

U.S. PATENT DOCUMENTS

| | | | |
|---|---|---|---|
| 3,673,616 A * | 7/1972 | Fedorov ................ | A61F 2/1608 623/6.51 |
| 5,769,890 A | 6/1998 | McDonald | |
| 6,197,057 B1 | 3/2001 | Peyman et al. | |
| 6,443,984 B1 * | 9/2002 | Jahn ...................... | A61F 2/1629 623/6.22 |
| 2002/0045937 A1 * | 4/2002 | Sarfarazi ............... | A61F 2/1613 623/6.11 |
| 2003/0060881 A1 | 3/2003 | Glick et al. | |
| 2003/0097177 A1 * | 5/2003 | Tran ....................... | A61F 2/161 623/6.47 |
| 2007/0129798 A1 | 6/2007 | Chawdhary | |
| 2007/0260309 A1 * | 11/2007 | Richardson .......... | A61F 2/1613 623/6.34 |
| 2009/0005865 A1 * | 1/2009 | Smiley .................. | A61F 2/1613 623/6.13 |
| 2009/0319040 A1 * | 12/2009 | Khoury ................. | A61F 2/1635 623/6.13 |
| 2010/0121444 A1 * | 5/2010 | Ben Nun ............... | A61F 2/1635 623/6.34 |
| 2015/0289970 A1 * | 10/2015 | Akura ................... | A61F 2/1694 623/6.37 |

FOREIGN PATENT DOCUMENTS

| | | | |
|---|---|---|---|
| DE | 19501444 A1 | 7/1996 | |
| FR | 2835177 A1 * | 8/2003 | ............... A61F 2/16 |
| JP | 2002360616 A | 12/2002 | |
| JP | 2002543920 A | 12/2002 | |

(Continued)

OTHER PUBLICATIONS

Abstract of Japanese Patent JP-2013123616A1 to Ichikawa published Jun. 2013.*

*Primary Examiner* — Paul Prebilic
(74) *Attorney, Agent, or Firm* — Bacon & Thomas, PLLC

(57) ABSTRACT

An intraocular lens includes a plurality of lenses with a rear lens portion disposed in a posterior capsule from which an eye lens is extracted and a front lens portion disposed at the front side inside the eye in relation to the rear lens portion, and a support portion of the front lens portion among the lenses has flexibility. Accordingly, when the inside of the user's eye moves, the support portion is bent, and hence the front lens portion moves. When the front lens portion moves so that the gap between the front lens portion and the rear lens portion changes, a focal distance of a lens system including the front lens portion and the rear lens portion changes. Accordingly, it is possible to realize an intraocular lens capable of changing a focal distance in a manner such that a user moves the inside of an eye.

15 Claims, 12 Drawing Sheets

(56) References Cited

FOREIGN PATENT DOCUMENTS

| | | | |
|---|---|---|---|
| JP | 2004515309 A | 5/2004 | |
| JP | 2007313326 A | 12/2007 | |
| JP | 2008526452 A | 7/2008 | |
| JP | 2009509636 A | 3/2009 | |
| JP | 2010502398 A | 1/2010 | |
| JP | 2011245322 A | 12/2011 | |
| JP | 2013123616 A1 * | 6/2013 | ................ A61F 2/16 |
| WO | WO01/08605 A1 * | 2/2001 | ............ A61F 2/1613 |

* cited by examiner

A-A CROSS SECTION

A-A CROSS SECTION

INTRAOCULAR LENS

BACKGROUND OF THE INVENTION

1. Field of the Invention

The present invention relates to an intraocular lens.

2. Description of the Related Art

As widely known, a surgery operation has been widely performed in which a cloudy white eye lens of a patient is extracted and an intraocular lens is inserted into an eye as the treatment for the eye's cataract. For example, Japanese Patent No. 2792588 below proposes an intraocular lens which is inserted into an eye from which an eye lens is extracted and is sutured to a ciliary body in the treatment of cataract.

SUMMARY OF THE INVENTION

It is important to focus on a visual object for the patient having an eye from which the eye lens is extracted and the intraocular lens is attached thereto. Even in the intraocular lens of the related art, it is possible to naturally focus on a visual object in a predetermined distance determined in response to a focal distance of the intraocular lens. However, the intraocular lens of the related art does not have a structure for adjusting a focal point with respect to a visual object in a distance different from the predetermined distance.

Therefore, an object of the invention is to provide an intraocular lens that is attached into an eye, from which an eye lens is extracted, and is able to adjust a focal point by a user.

In order to solve the above-described problems, according to the invention, there is provided an intraocular lens including: a rear lens portion which has a lens function and is received in a posterior capsule inside an eye from which an eye lens is extracted while at least the posterior capsule is left; and a front lens portion which has a lens function and is disposed at the front side inside the eye in relation to the rear lens portion, wherein the front lens portion includes a first lens which is disposed at a position facing a lens surface of a second lens as a lens of the rear lens portion, and a support portion which extends from a limbus of the first lens to a position of a part of a region from an iris to a ciliary body inside the eye, supports the first lens, and has flexibility, and wherein the support portion includes an extension portion which is formed in a shape extending toward the lateral side of the first lens and supports the first lens while a portion farthest from the center of the first lens in the shape comes into contact with the inside of a ciliary sulcus of the eye, and a sub-extension portion which is branched from a side surface of the extension portion, extends toward the rear side inside the eye, and comes into contact with a surface of the ciliary body so that a force of pressing the first lens toward the front side inside the eye is transmitted when the sub-extension portion is pressed by the ciliary body while the first lens is disposed at a rear section of the eye.

Accordingly, the intraocular lens according to the invention is the intraocular lens with a plurality of lenses with the rear lens portion disposed in the posterior capsule from which the eye lens is extracted and the front lens portion disposed at the front side inside the eye in relation to the rear lens portion, and the support portion of the front lens portion has flexibility. Thus, when the inside of the user's eye moves, the support portion is bent, and hence the front lens portion moves. When the front lens portion moves so that the gap between the front lens portion and the rear lens portion changes, a focal distance of a lens system including the front lens portion and the rear lens portion changes. Accordingly, it is possible to realize an intraocular lens capable of changing a focal distance in a manner such that a user moves the inside of an eye.

Further, one of the first lens and the second lens may be a convex lens and the other thereof may be a concave lens.

According to the invention, since one of the first lens and the second lens is the convex lens and the other thereof is the concave lens, it is possible to realize an intraocular lens capable of adjusting a focal distance in a wide range from a near position to a far position by changing a distance between a long-sight convex lens and a short-sight concave lens in combination thereof.

Further, the support portion may have a bent shape in which the support portion is bent in response to the movement of the region from the iris to the ciliary body while a front end of the support portion comes into contact with a position of a part of the region from the iris to the ciliary body inside the eye so that the first lens is movable inside the eye in the front and rear direction.

According to the invention, the flexible support portion has a bent shape. Thus, when a region from the iris to the ciliary body moves by the bent shape, the support portion is bent, and hence the first lens moves inside the eye in the front and rear direction. Accordingly, it is possible to adjust the focal distance by effectively moving the front lens portion in the front and rear direction by the bent shape of the support portion.

Further, the support portion may include a nipping portion which is formed in a shape extending toward the lateral side of the first lens disposed at the rear section and nips a part of the rear section side of the iris of the eye so as to support the first lens.

According to the invention, the support portion of the front lens portion includes the nipping portion which nips a part of the rear section side of the iris of the eye. Accordingly, since a part of the rear section side of the iris is nipped, the front lens portion may be reliably supported inside the eye.

Further, the shape of the nipping portion may be a shape in which a portion nipping the iris in the nipping portion is located at the front side inside the eye in relation to the first lens.

According to the invention, since the shape of the nipping portion is formed as the shape in which a portion nipping the iris is located at the front side inside the eye in relation to the lens portion, the first lens may be located at the further rear side while the first lens is fixed to the rear section inside the eye by the nipping portion, and hence an enough gap may be provided between the first lens and the iris. Thus, it is possible to effectively suppress the adhesion between the first lens and the iris.

Further, the support portion may include an extension portion which is formed in a shape extending toward the lateral side of the first lens and supports the first lens while a portion farthest from the center of the first lens in the shape comes into contact with the inside of a ciliary sulcus of the eye.

According to the invention, the structure which supports the front lens portion has a structure which extends toward the lateral side of the first lens and supports the front lens portion while coming into contact with the inside of the ciliary sulcus. Accordingly, the front lens portion is effectively supported by the structure coming into contact with the inside of the ciliary sulcus.

Further, the extension portion may have a bent shape, and the bent shape may be a shape in which the first lens is movable inside the eye in the front and rear direction in response to the movement of the ciliary sulcus while a portion farthest from the center of the first lens in the extension portion comes into contact with the inside of the ciliary sulcus of the eye.

According to the invention, the extension portion has a shape in which the front lens portion moves inside the eye in the front and rear direction when the ciliary body moves while the extension portion is fixed to the ciliary sulcus. Thus, when a patient moves the ciliary body in order to perform the focusing operation of the eye, the front lens portion moves in the front and rear direction in response to the movement of the ciliary body. Accordingly, there is a possibility that the intraocular lens capable of performing the focusing operation of the eye in response to the distance to the object may be realized.

Further, the extension portion may have flexibility and may have a size in which at least a part of the extension portion is bent while a portion farthest from the center of the first lens in the extension portion comes into contact with the inside of the ciliary sulcus of the eye.

According to the invention, the extension portion has flexibility and the size thereof is set to a size in which at least a part of the extension portion is bent while the extension portion is inserted into the ciliary sulcus in a contact state. Accordingly, since the extension portion presses the inside of the ciliary sulcus by a certain degree of a force, it is possible to effectively prevent the front end of the extension portion from being deviated from the ciliary sulcus and hence to reliably fix the intraocular lens to the rear section.

Further, the extension portion may include a plurality of leg portions which extends from a plurality of positions of the limbus of the first lens in the circumferential direction in a direction moving away from the center of the first lens due to the leg shape.

According to the invention, since the extension portion is formed as a plurality of leg portions having leg shapes, it is possible to realize an intraocular lens which is reliably fixed to the rear section by a simple structure and shape.

Further, a front end of the leg portion may come into contact with at least a part of a deep portion of the ciliary sulcus while being inserted into the ciliary sulcus of the eye.

According to the invention, since the extension portion is formed as a plurality of leg portions having leg shapes and the front end of the leg portion comes into contact with the inside of the ciliary sulcus, it is possible to reliably fix the intraocular lens to the rear section by a simple structure with a leg-shaped portion and a simple method of causing the front end thereof to come into contact with the inside of the ciliary sulcus.

Further, the leg portion may include a bent portion which is bent at a position between an end close to the first lens and an end far from the first lens in the leg shape, and the leg portion may have a shape in which the end close to the first lens in the leg portion is located at the front side of the eye in relation to the bent portion and the end far from the first lens in the leg portion is located at the front side of the eye in relation to the bent portion so that the first lens is pressed toward the front side inside the eye when the ciliary sulcus presses the leg portion while the first lens is disposed at the rear section of the eye.

According to the invention, the shape of the leg portion is specifically formed as a shape which extends from a position near the lens portion toward the rear side inside the eye and is bent so as to extend toward the front side inside the eye. Due to such a bent shape, the lens portion moves in the front and rear direction when the patient moves the ciliary sulcus so as to focus on the visual object, and hence an intraocular lens capable of performing a focusing operation of an eye in response to a distance to an object may be realized.

Further, the extension portion may include an annular ring portion which is inserted into the ciliary sulcus in the circumferential direction.

According to the invention, since the extension portion includes the annular ring portion which is inserted into the ciliary sulcus in the circumferential direction, the extension portion may come into contact with the inside of the ciliary sulcus in a wide range of the ciliary sulcus in the circumferential direction when the extension portion is inserted into the ciliary sulcus. Thus, the front lens portion may be reliably fixed to the rear section.

Further, a portion coming into contact with the inside of the ciliary sulcus in the extension portion may be provided with a concave portion or a convex portion which is fitted to an uneven portion inside the ciliary sulcus.

According to the invention, since a portion coming into contact with the inside of the ciliary sulcus in the extension portion is provided with the concave portion or the convex portion and the concave portion or the convex portion is fitted to the uneven portion inside the ciliary sulcus, the extension portion may be further reliably fixed into the ciliary sulcus by the fitting to the uneven portion of the ciliary sulcus.

Further, the front lens portion may include a sub-extension portion which extends from the lateral side of the first lens and comes into contact with the surface of the ciliary body.

According to the invention, since the sub-extension portion is provided which extends from the lateral side of the first lens and comes into contact with the surface of the ciliary body, the intraocular lens may be reliably fixed into the eye by using the ciliary body without suturing.

Further, the sub-extension portion may have a shape which extends from the lateral side of the first lens toward the rear side inside the eye so that a force of pressing the first lens toward the front side inside the eye is transmitted when the sub-extension portion is pressed by the ciliary body while the first lens is disposed at the rear section of the eye.

According to the invention, the sub-extension portion which comes into contact with the surface of the ciliary body extends from the lateral side of the first lens toward the rear side inside the eye. Accordingly, when the sub-extension portion is pressed by the ciliary body, a force of pressing the first lens toward the front side inside the eye is transmitted. Thus, when the patient moves the ciliary body so as to perform the focusing operation of the eye, the lens portion moves in response to the movement of the ciliary body. Accordingly, it is possible to realize an intraocular lens capable of performing a focusing operation of an eye in response to a distance to an object.

DETAILED DESCRIPTION OF THE PREFERRED EMBODIMENTS

Figure 1:
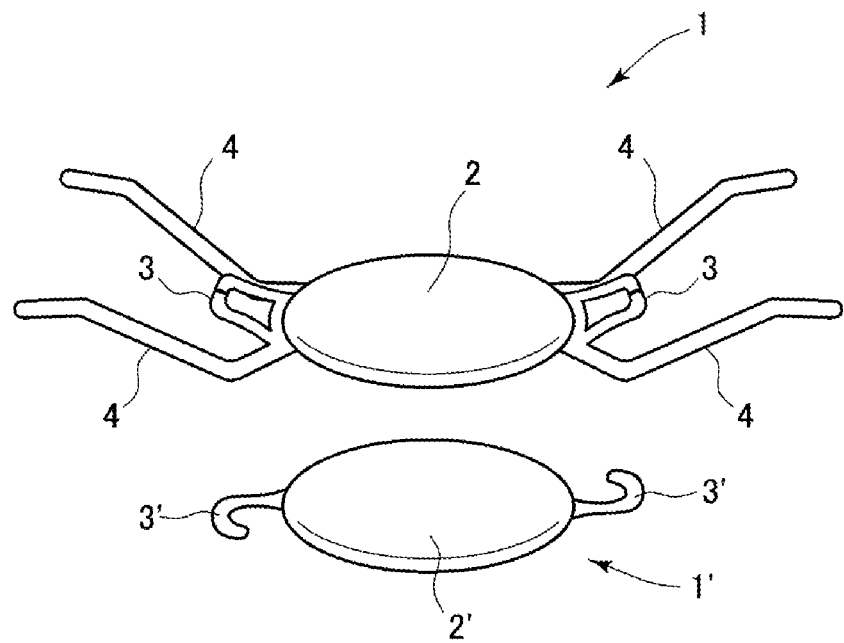
FIG. 1 is a perspective view illustrating an intraocular lens of a first embodiment of the invention.
Figure 2:
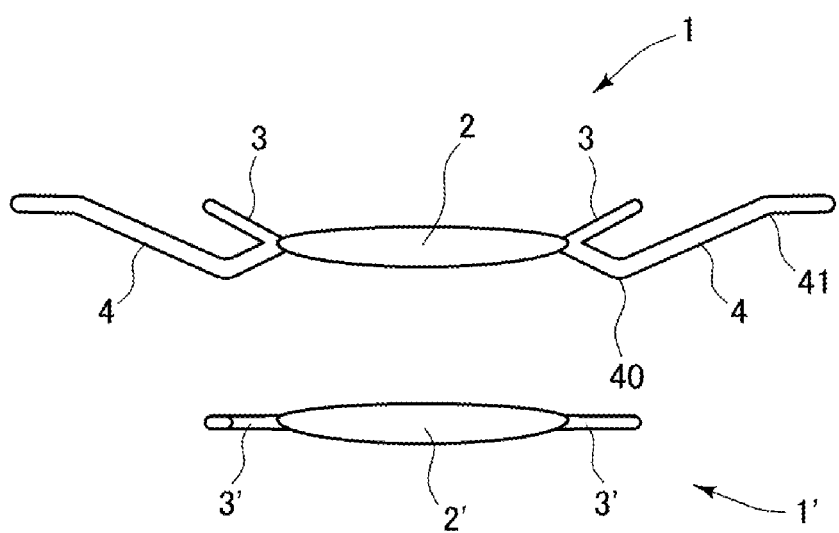
FIG. 2 is a side view illustrating the intraocular lens of the first embodiment.
Figure 3:
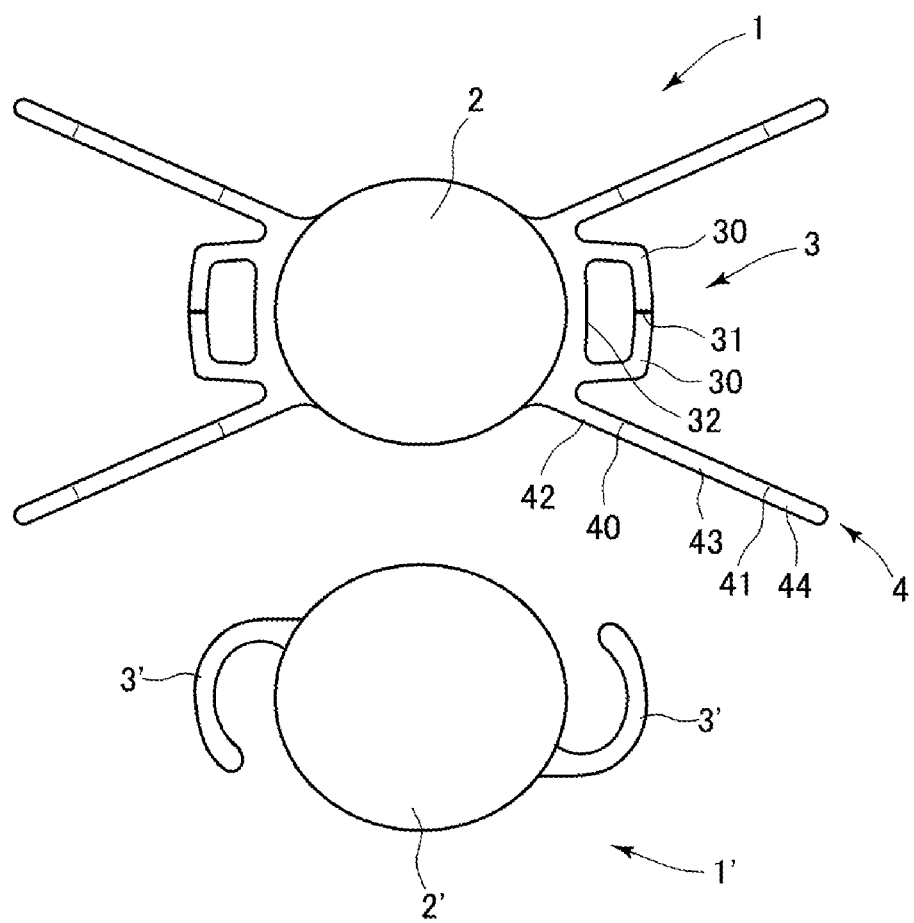
FIG. 3 is a front view illustrating the intraocular lens of the first embodiment.

Hereinafter, embodiments of the invention will be described with reference to the drawings. First, FIGS. 1 to 3 are a perspective view, a side view, and a front view illustrating an intraocular lens of the invention (the description on the direction such as a side surface or a front surface indicates the direction (the side surface or the front surface) of a patient's face (or eye)).

As illustrated in the drawings, the intraocular lens includes two lenses, that is, a front lens portion 1 which is disposed at the relatively front side inside the eye and a rear lens portion 1' which is disposed at the relatively rear side inside the eye. The front lens portion 1 and the rear lens portion 1' are formed separately from each other. Both the front lens portion 1 and the rear lens portion 1' are disposed at the rear section (behind an iris) inside the eye from which an eye lens is extracted due to, for example, cataract. Here, the eye lens is extracted in a state where a posterior capsule is left (external extraction surgery).

The front lens portion 1 is disposed at the front side of the posterior capsule. As will be described later, the front lens portion 1 has a structure in which the front lens portion holds the iris in a nipped state and a structure in which the front lens portion is inserted into a ciliary sulcus and comes into contact with a deep portion (a structure in which the front lens portion further comes into contact with a surface of a ciliary body), and hence the front lens portion is fixed to a rear section (without suturing) by these structures. The rear lens portion 1' is received inside the posterior capsule, and is stably held inside the posterior capsule while coming into contact with the inner surface of the posterior capsule.

The front lens portion 1 includes a lens 2 (a first lens), a nipping portion 3, and a leg portion 4 (an extension portion). The lens 2 is disposed in the rear section of the eye (the section behind the iris) after the eye lens becoming cloudy white due to, for example, the cataract is extracted from the patient's eye, and serves as the eye lens.

The nipping portion 3 supports and fixes the lens 2 in the rear section by nipping the iris therebetween. The nipping portion 3 includes a pair of arms 30 and 30. As illustrated in FIG. 2, the arms 30 and 30 extend from both right and left limbuses of the lens 2 and are bent at the half portion thereof. Here, the arms are formed so that front ends 31 and 31 of both arms 30 and 30 contact each other when the iris is not nipped therebetween.

The nipping portion 3 is formed of a material having elasticity (flexibility and bendability). Here, a doctor (an operator) may elastically deform the nipping portion 3 so that a part of a portion contacting the rear section of the iris is nipped between the front ends 31 and 31 of the arms 30 and 30. Accordingly, the iris is continuously nipped between the arms 30 and 30 due to the elastic restoration force thereof. When the same nipping operation is performed by the nipping portions 3 formed at the right and left sides of the intraocular lens in the drawing, the lens 2 is supported in the rear section.

As illustrated in FIG. 2, the pair of arms 30 and 30 of the nipping portion 3 may have a shape in which the arms obliquely extend from the limbus of the lens 2 toward the front side of the eye (that is, the front ends 31 of the arms 30 and 30 are located at the front side in relation to the root side) (as described above, the description on the front side or the rear side also indicates the front side or the rear side of the patient's face in which the front lens portion 1 is attached into the eye). Accordingly, a gap may be formed between the lens 2 and the iris as will be described later. This exhibits an important effect of preventing (suppressing) the adhesion between the lens 2 and the iris.

In the embodiment of FIGS. 1 to 3, the leg portion 4 has a structure with four legs. Each of the four legs includes bent portions 40 and 41, a root portion 42 which is located near the lens 2 in relation to the bent portion 40, an intermediate portion 43 which is located between the bent portions 40 and 41, and a front end 44 which is located near the front end in relation to the bent portion 41. As illustrated in FIG. 2, the root portion 42 has a shape in which the root portion extends backward in relation to the lens 2 (the bent portion 40 is located at the rear side in relation to the lens 2). The intermediate portion 43 has a shape in which the intermediate portion extends from the bent portion 40 toward the front side of the eye (the bent portion 41 is located at the front side inside the eye in relation to the bent portion 40). The front end 44 has a shape in which the front end extends (substantially) in parallel to the lens.

Furthermore, the leg portion 4 of FIGS. 1 to 3 is not limited to one example. As will be described later, in the invention, the leg portion 4 may have various shapes. The nipping portion 3 and the leg portion 4 may be formed of, for example, a resin material or the like so as to be integrated with the lens 2. Alternatively, the nipping portion and the leg portion may be formed separately from the lens 2 and then may be coupled (stuck) to each other.

The lower portions of FIGS. 1 to 3 illustrate the rear lens portion 1'. As described above, the rear lens portion 1' is received inside the posterior capsule from which the eye lens is extracted. As illustrated in the drawings, it is desirable that the lens 2 of the front lens portion 1 and a lens 2' of the rear lens portion 1' be separated from each other and be disposed so that the lens surfaces (the curved surfaces of the lenses)

thereof face each other. At that time, it is desirable to dispose the optical axes of the lens 2 and the lens 2' so that the optical axes overlap the eye's visual axis.

The rear lens portion 1' includes the lens 2' (the second lens) having a lens function and a loop portion 3'. In the examples of FIGS. 1 to 3, a pair of the loop portions 3' is formed at the limbus of the lens 2' at the opposite side in the optical axis. The loop portion 3' has a loop shape and has flexibility (elasticity). In the state where the rear lens portion 1' is received inside the posterior capsule, the pair of loop portions 3' is bent, and the posterior capsule is pressed from the inside by an elastic restoration force, so that the arrangement position of the rear lens portion 1' is fixed. The loop portion 3' may be integrally molded with the lens 2' or may be formed as separate members so that the separate members are bonded (for example, stuck) to each other.

The lens 2 of the front lens portion 1 and the lens 2' of the rear lens portion 1' may be any one of a plus lens (a convex lens) and a minus lens (a concave lens). That is, the lens 2 may be formed as the plus lens and the lens 2' may be formed as the minus lens. Further, the lens 2 may be formed as the minus lens and the lens 2' may be formed as the plus lens. Further, both the lens 2 and the lens 2' may be formed as the plus lenses or the minus lenses. Furthermore, the plus lens (the convex lens) may be any one of a biconvex lens, a planoconvex lens, and a meniscus lens, and the minus lens (the concave lens) may be any one of a biconcave lens, a planoconcave lens, and a meniscus lens.

As widely known, a focal distance of a lens system including the front lens portion 1 and the rear lens portion 1' is determined in response to the focal distances of both lenses and the distance between both lenses. As will be described later, in the intraocular lens of the invention, the position of the lens 2 of the front lens portion 1 is movable in the front and rear direction, and hence the distance between both lenses changes. Accordingly, the focal distance of the lens system including both lenses changes. Accordingly, there is a possibility that a user who wears the intraocular lens of the invention may adjust the focal distance of the intraocular lens in response to the distance to the visual object. In particular, in the case where one of the lens 2 and the lens 2' is formed as a short-sight minus lens and the other thereof is formed as a long-sight plus lens, the possibility of widening the focal point adjustable range is improved.

Figure 4:
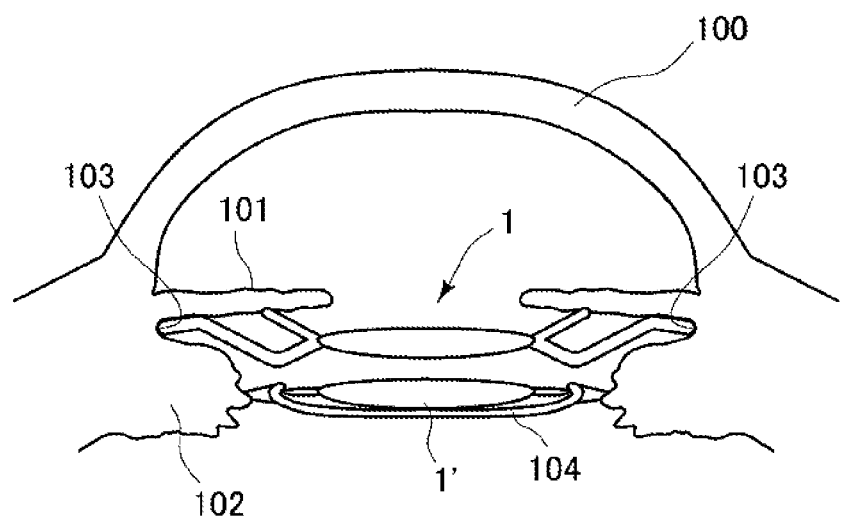
FIG. 4 is a view illustrating a state where the intraocular lens is inserted and fixed into an eye.

FIG. 4 is a cross-sectional view of the eye to which the front lens portion 1 and the rear lens portion 1' of FIGS. 1 to 3 are attached (fixed). As widely known, the front side of an iris 101 inside the eye is called a front section and the rear side thereof is called a rear section. However, the front lens portion 1 is disposed at the rear section among these sections. A ciliary body 102 exists at the rear side of the iris 101, and the eye lens is normally supported at the center side of the ciliary body 102 inside the eye. A groove-shaped area which is continuously formed between the iris 101 and the ciliary body 102 in the circumferential direction is called a ciliary sulcus 103.

First, the eye lens which becomes cloudy white due to the cataract is extracted while the posterior capsule 104 is left (extracapsular extraction surgery). Then, a part of a cornea 100 is incised, and the rear lens portion 1' is inserted therethrough so that the loop portion 3' is received inside the capsule in a bent state. For example, the rear lens portion 1' is rolled and inserted into a cartridge by using the elasticity (bendability) of the rear lens portion 1', the front end of the cartridge reaches the inside of the posterior capsule 104 through the cornea 100, and then the rear lens portion 1' is discharged thereto. Next, the front lens portion 1 is inserted into the rear section. Even at that time, for example, the front lens portion 1 is rolled and inserted into a cartridge by using the elasticity (bendability) of the front lens portion 1, the front end of the cartridge reaches the rear section through the cornea 100, and then the front lens portion 1 is discharged thereto.

In order to fix the front lens portion 1 to the rear section, the iris is nipped by the nipping portion 3, and the leg portion 4 is inserted and fixed into the ciliary sulcus 103. At the side of the nipping portion 3, a part of the rear surface of the iris is nipped so that the arms of the both nipping portions 3 and 3 pluck the rear surface. Further, at the side of the leg portion 4, the front end of the leg portion 4 is fixed to the deepest portion of the ciliary sulcus 103 in a contact state. Furthermore, the contact target of the front end of the leg portion 4 may not be the deepest portion of the ciliary sulcus 103. For example, the front end of the leg portion 4 may come into contact with at least a part inside the ciliary sulcus 103.

As a major point of the invention, any portion of the front lens portion 1 including the nipping portion 3 and the leg portion 4 is not sutured into the eye. Further, it is desirable to design the length of the leg portion 4 in a degree that the leg portion 4 is slightly bent while the front end of the leg portion 4 is inserted into the ciliary sulcus 103. As described above, the front lens portion 1 is reliably fixed to the rear section by a complex fixing method using two kinds of fixing members, that is, the nipping portion and the leg portion. Further, the rear lens portion 1' is also stably held inside the posterior capsule by the loop portion 3'.

The front lens portion 1 of the invention has a function capable of moving the position of the lens 2 in the front and rear direction by the action (the reflex action) in which the patient's eye tries to focus on an object. The function will be described with reference to FIG. 5.

Figure 5:
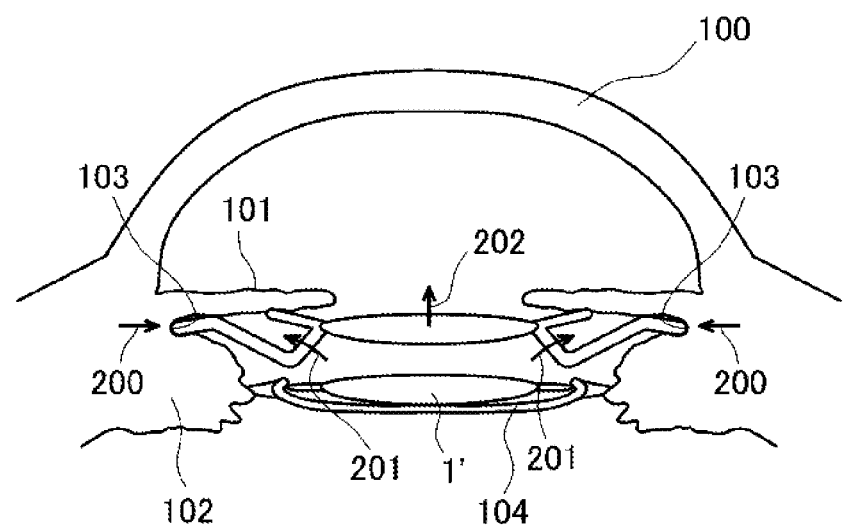
FIG. 5 is a side view illustrating an example of a state where the intraocular lens moves.

According to the medical knowledge, a force is exerted in the direction indicated by the arrow 200 of FIG. 5 in the case where a human's eye tries to focus on an object. This force twists the leg portion 4 of the front lens portion 1 as illustrated in FIG. 5. That is, the bent portion 41 is pressed toward the lens 2, and the root portion 42 and the intermediate portion 43 of the leg portion 4 change to a posture in which the root portion 42 and the intermediate portion 43 become more perpendicular to the lens 2.

Accordingly, the posture of the root portion 42 changes in the direction of the arrow 201, and hence the lens 2 is pressed toward the front side inside the eye. When the force of the arrow 200 disappears, the lens 2 returns to the original position. In this way, when the lens 2 moves in the front and rear direction, the distance between the lens 2 and the lens 2' changes. As widely known, when the distance between two lenses changes, the focal distance of the lens system including two lenses also changes. Accordingly, when the patient having an eye into which the front lens portion 1 and the rear lens portion 1' of the invention are attached moves the ciliary sulcus in order to focus on the visual object, the focal distance of the intraocular lens may be adjusted depending on the visual object.

FIGS. 6 to 11 illustrate different embodiments of the intraocular lens of the invention. Furthermore, in the embodiments below, the same reference numerals will be given to the same components as those of FIGS. 1 to 3, and the repetitive description thereof will not be presented.

Figure 6:
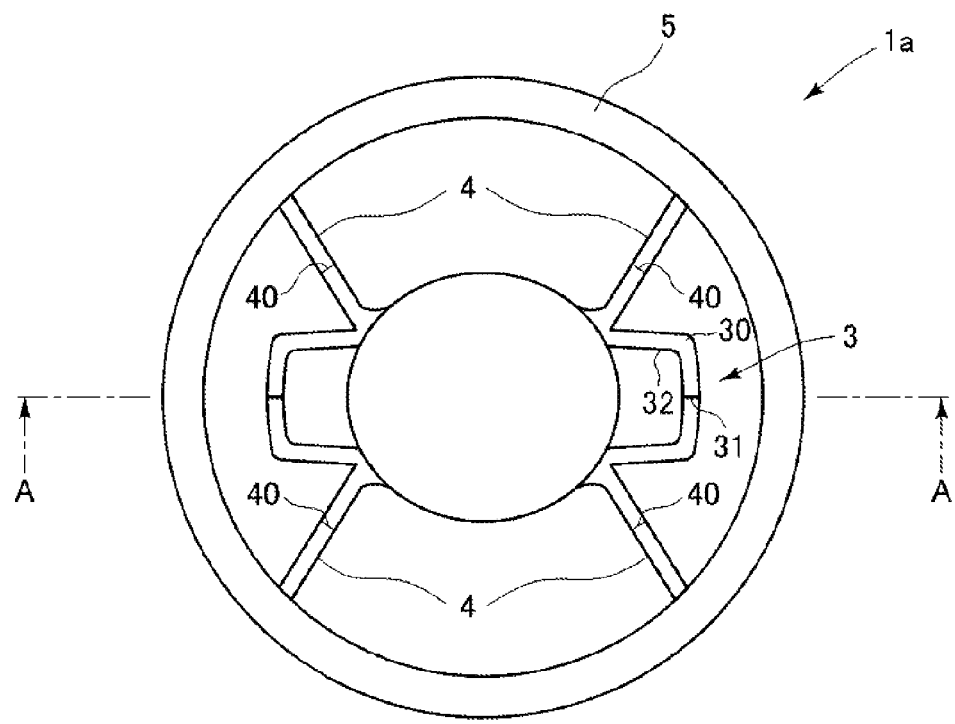
FIG. 6 is a front view illustrating a front lens portion of a second embodiment.
Figure 7:
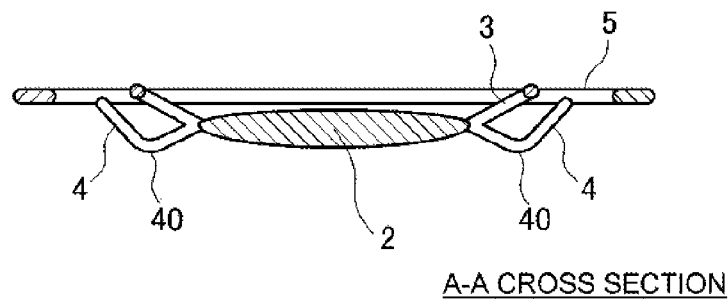
FIG. 7 is a cross-sectional view illustrating the front lens portion of the second embodiment.

A front lens portion 1a of a second embodiment of FIGS. 6 and 7 is an example in which a ring portion 5 is formed in the circumferential direction so that the front ends of the leg portions 4 are connected to the ring portion. In this example, the leg portion includes the bent portion 40 as in the case of FIG. 1 and the like. Here, the leg portion 4 first extends from the limbus of the lens 2 or the nipping portion 3 toward the rear side inside the eye and is bent at the bent portion 40 so as to be directed toward the ring portion 5 located at the front side inside the eye.

As illustrated in FIG. 7, the ring portion 5 has a cross-sectional shape in which the ring portion is short and flat in the visual axis direction (for example, the up and down direction of FIG. 2) of the eye. The front lens portion 1a of the second embodiment of FIGS. 6 and 7 may be disposed such that a part of the rear surface of the iris is nipped by the nipping portion 3, the ring portion 5 is inserted into the ciliary sulcus 103 along the entire circumference thereof, and the outer end of the ring portion 5 in the radial direction comes into contact with, for example, the deepest portion of the ciliary sulcus 103. Since the ring portion 5 comes into contact with the ciliary sulcus along the entire circumference thereof, the ring portion is stably fixed. At that time, it is desirable that the ring portion 5 has a flat shape in that the ring portion may be suitably inserted into the ciliary sulcus.

Figure 8:
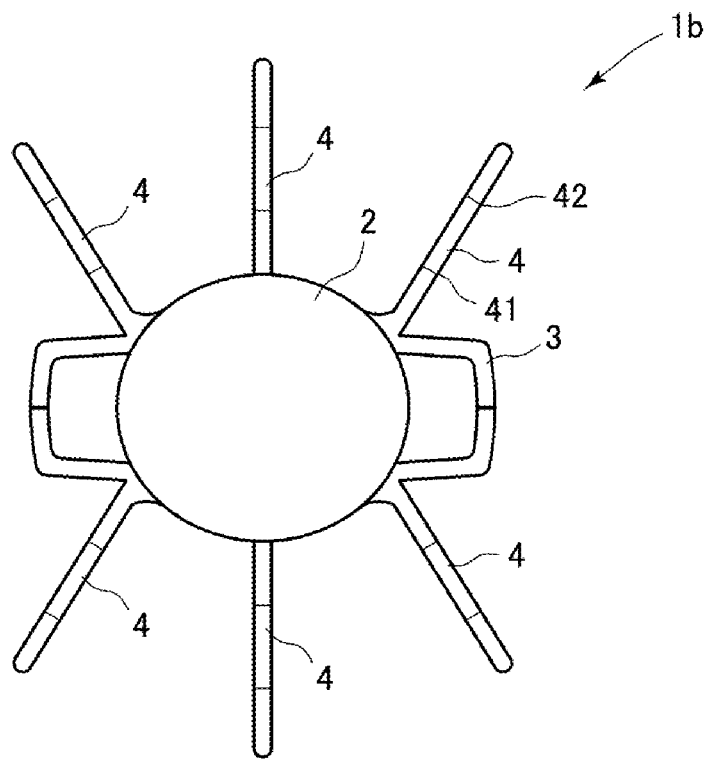
FIG. 8 is a front view illustrating a front lens portion of a third embodiment.

FIG. 8 illustrates a front lens portion 1b of a third embodiment. The example of FIG. 8 is an example in which six leg portions 4 are provided. Even in this example, the front ends of six leg portions 4 are inserted and fixed into the deepest portion of the ciliary sulcus. The invention is not limited to the case where four leg portions 4 are provided as illustrated in FIG. 1 and six leg portions 4 are provided as illustrated in FIG. 8. For example, an arbitrary (even) number of the leg portions 4 may be provided so that eight or ten leg portions are provided.

Figure 9:
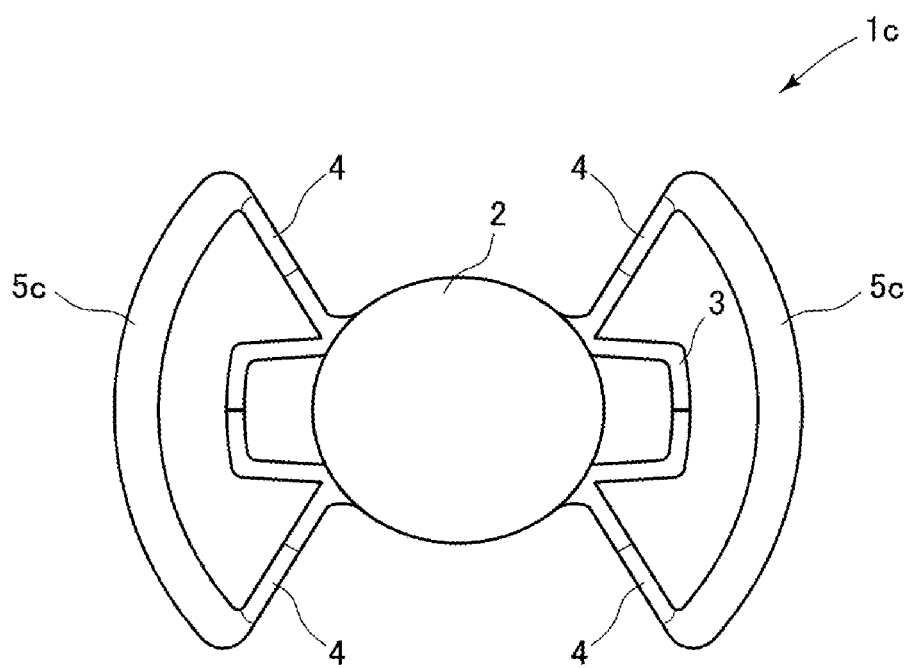
FIG. 9 is a front view illustrating a front lens portion of a fourth embodiment.

FIG. 9 illustrates a front lens portion 1c of a fourth embodiment. The front lens portion 1c is an example in which the ring portion 5 of FIG. 5 is not formed in the entire circumference. In this example, a circular-arc portion 5c is formed so as to connect the front ends of the leg portions 4 which are adjacent to each other at both right and left sides of the nipping portion 3. The invention is not limited to this example. For example, in the invention, only a part of the ring portion of FIG. 6 may be formed.

Figure 10:
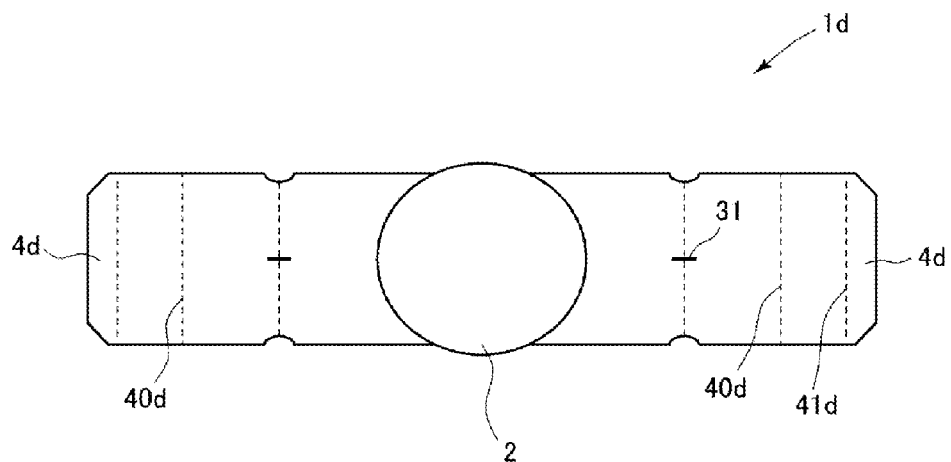
FIG. 10 is a front view illustrating a front lens portion of a fifth embodiment.

FIG. 10 illustrates a front lens portion 1d of a fifth embodiment. The front lens portion 1d has a structure in which the leg portion and the nipping portion are commonly used. Specifically, a plate-shaped portion 4d which has substantially the same width as the lens 2 and has a thin plate shape (a flat shape) in the thickness direction (the visual axis direction) is provided at each of the right and left sides of the lens 2. A notched portion 31 is provided in the vicinity of the middle position of the plate-shaped portion 4d, and nips the rear side of the iris so that a nipping portion is formed. Further, the front end side of the plate-shaped portion 4d corresponds to the leg portion, and the front end comes into contact with, for example, the deepest portion of the ciliary sulcus. That is, the front lens portion of the invention includes a plate-shaped portion which is commonly used as the extension portion and the nipping portion. Here, the nipping portion is a notched portion which is formed at the intermediate portion (which may not be limited to the middle position) of the plate-shaped portion so as to nip the iris, and the front end of the plate-shaped portion may come into contact with the inside of the ciliary sulcus.

The plate-shaped portion 4d may have a shape in which a flat plate is bent at three positions. That is, in FIG. 10, the dashed line intersecting the notched portion 31 is a bending line which protrudes toward the front side inside the eye, the dashed line 40d is a bending line which protrudes toward the rear side inside the eye, and the dashed line 41d is a bending line which protrudes toward the front side inside the eye.

Then, the front end side of the dashed line 41d may extend in the transverse direction (the direction perpendicular to the visual axis).

With the above-described shape, since the notched portion 31 protrudes toward the front side inside the eye, the iris may be easily nipped and the front end side of the dashed line may be easily inserted into the ciliary sulcus. Further, since the bending lines are provided at three positions, the lens 2 moves forward when the force of the arrow 200 is exerted as illustrated in FIG. 5, and the lens 2 returns backward as the force disappears. In the case of the shape of FIG. 10, since the leg portion is formed in a thick size, the strength is improved.

Figure 11:
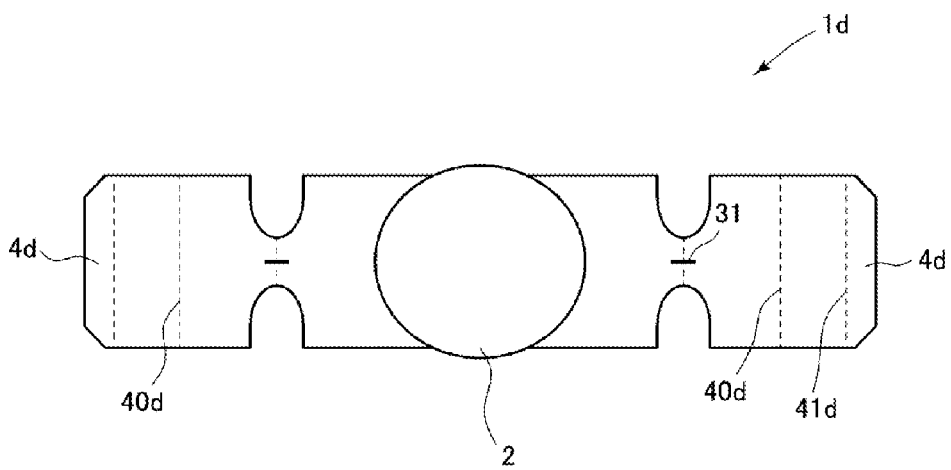
FIG. 11 is a front view illustrating a front lens portion of a sixth embodiment.

The front lens portion 1d of FIG. 10 may be deformed as illustrated in FIG. 11. In a sixth embodiment of FIG. 11, the plate-shaped portion 4d is formed in a shape in which the periphery of the notched portion 31 is deeply recessed. In the case of this shape, since it is possible to prevent an unnecessary portion from contacting the iris or to be easily bent at the notched portion 31, a nipping operation is reliably performed by the notched portion 31.

In the intraocular lens of the invention, the front end shape of the leg portion may be various. FIGS. 12 to 15 illustrate four examples of the front end shape of the leg portion.

Figure 12:
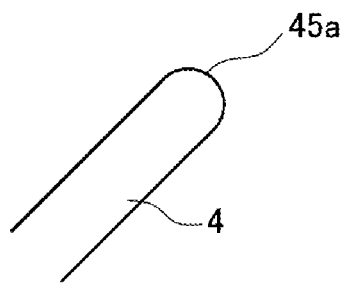
FIG. 12 is a view illustrating a first example of a front end of a leg portion.
Figure 13:
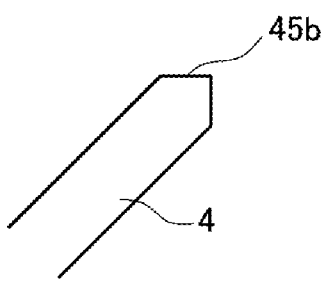
FIG. 13 is a view illustrating a second example of the front end of the leg portion.

In the example of FIG. 12, a front end 45a of the leg portion 4 has a curved surface shape. In this example, the curved surface comes into plane-contact with the deepest portion (the inside) of the ciliary sulcus, and hence the leg portion 4 is reliably fixed to the ciliary sulcus. In the example of FIG. 13, a front end 45b of the leg portion 4 is formed in a sharp shape with a corner. In this example, the corner is pressed against the deepest portion (the inside) of the ciliary sulcus, and hence the leg portion 4 is reliably fixed to the ciliary sulcus.

Figure 14:
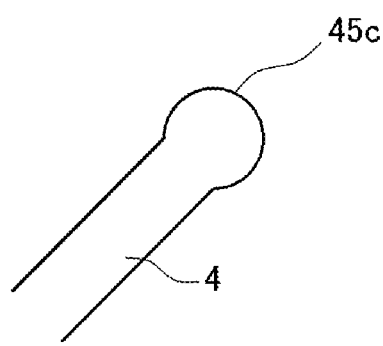
FIG. 14 is a view illustrating a third example of the front end of the leg portion.
Figure 15:
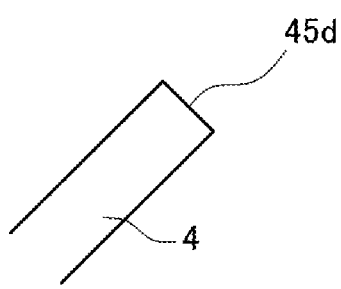
FIG. 15 is a view illustrating a fourth example of the front end of the leg portion.

In the example of FIG. 14, a front end 45c of the leg portion 4 is formed in a spherical shape. In this example, the front end comes into plane-contact with the deepest portion (the inside) of the ciliary sulcus by the spherical shape thereof, and hence the leg portion 4 is reliably fixed to the ciliary sulcus. In the example of FIG. 15, a front end 45d of the leg portion 4 is formed in a plane shape. In this example, the front end comes into plane-contact with the deepest portion (the inside) of the ciliary sulcus, and hence the leg portion 4 is reliably fixed to the ciliary sulcus.

Furthermore, the leg portions 4 of FIGS. 12 to 15 have plate shapes (flat shapes), and only the surfaces perpendicular to the visual axis may be illustrated in FIGS. 12 to 15. In that case, for example, the front end 45b of FIG. 13 comes into line-contact with the deepest portion of the ciliary sulcus.

In the intraocular lens of the invention, the front end shape of the leg portion may be modified as below. This modification will be described with reference to FIGS. 16 to 18.

Figure 16:
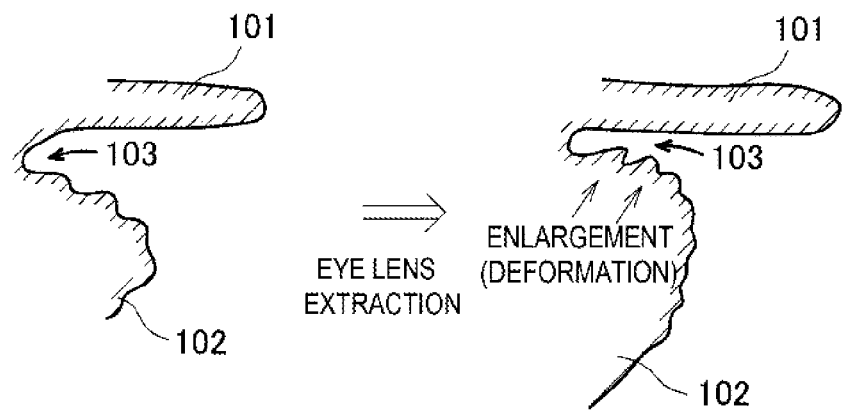
FIG. 16 is a view illustrating an example of the state of a ciliary body and a ciliary sulcus after an eye lens is extracted.

According to the new knowledge obtained by the inventor, there is a tendency that the ciliary body 102 is enlarged (deformed) after the eye lens is extracted. In the enlargement (deformation), for example, as illustrated in FIG. 16, the ciliary sulcus 103 is deformed so as to be narrowed. Accordingly, the uneven shape which exists on the surface of the ciliary sulcus becomes closer to the iris 101.

Figure 17:
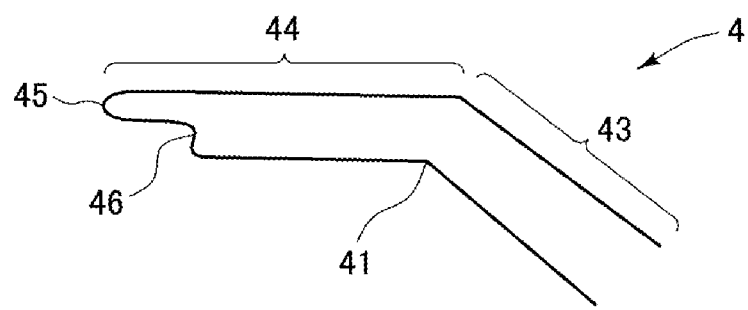
FIG. 17 is a view illustrating an example of a concave portion of the front end of the leg portion.

In order to handle this deformation (or use this deformation), it is desirable to form a concave portion 46 in the vicinity of the front end 45 of the leg portion 4 as illustrated in FIG. 17. The formation position of the concave portion 46 becomes a position opposite to the iris (a position facing the ciliary body) in the leg portion 4 when the leg portion is fixed into the eye. That is, the formation position may be a position close to the front end in a degree that the concave portion comes into contact with the enlarged (deformed) ciliary sulcus.

Figure 18:
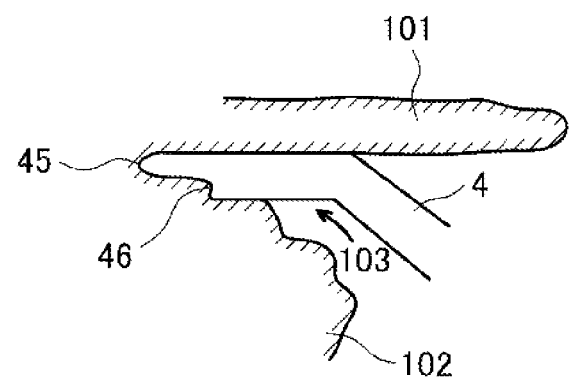
FIG. 18 is a view illustrating a function of the concave portion of the front end of the leg portion.

Accordingly, as illustrated in FIG. 18, a convex portion of the ciliary body 102 is inserted into the concave portion 46 of the leg portion 4, and hence the leg portion 4 is further reliably fixed to the ciliary sulcus. Even in the leg portions of FIGS. 1 and 12 to 15, the leg portion 4 having a different shape, the ring portion of FIG. 7, or the circular-arc portion of FIG. 9, the concave portion 46 may exhibit the function illustrated in FIG. 18 when the concave portion is formed in (the vicinity of) the front end thereof. Further, the invention is not limited to the case of forming the concave portion. For example, an uneven portion (or a concave portion and a convex portion) may be formed so as to be fitted to the uneven shape inside the ciliary sulcus 103.

In the above-described front lens portion, the structure (the leg portion, the ring portion, and the like) coming into contact with the inside of the ciliary sulcus is formed, but the front lens portion of the invention is not limited thereto. For example, a structure coming into contact with the ciliary body may be formed. The example is illustrated in FIGS. 19 to 25.

Figure 19:
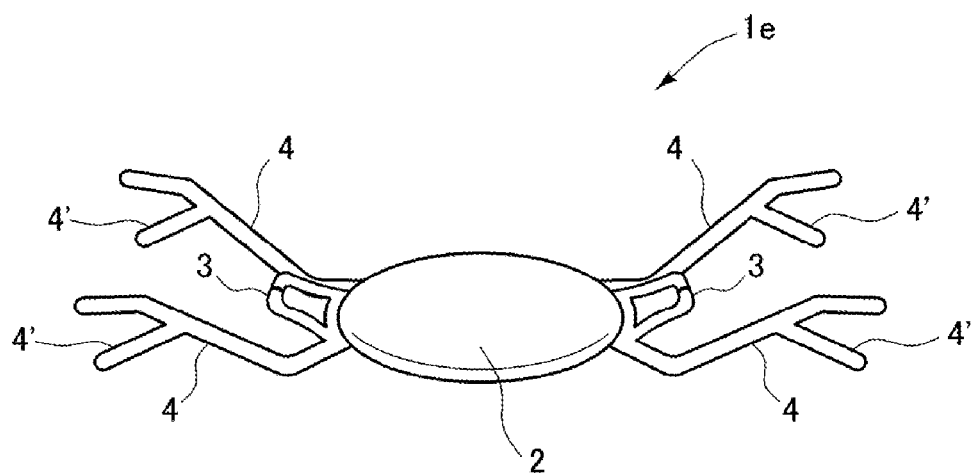
FIG. 19 is a perspective view illustrating a front lens portion of a seventh embodiment.
Figure 20:
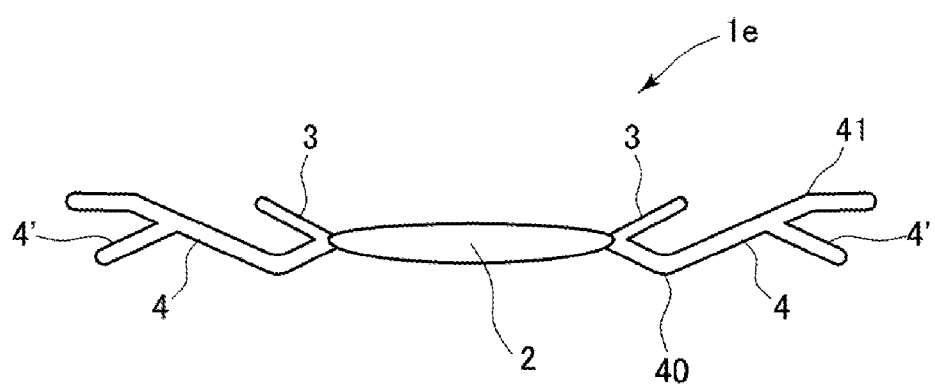
FIG. 20 is a side view illustrating the front lens portion of the seventh embodiment.

FIG. 19 is a perspective view illustrating a front lens portion 1e of a seventh embodiment, and FIG. 20 is a side view thereof. The front lens portion 1e includes a sub-leg portion 4' which is divided from the side surface of the intermediate portion 43 of the leg portion 4 and obliquely extends toward the rear side inside the eye. The front view of the front lens portion 1e may be, for example, the same as FIG. 3. That is, the extension direction when viewed from the front surface of the sub-leg portion 4' may be the same direction as that of the leg portion 4. Alternatively, the extension direction when viewed from the front surface of the sub-leg portion 4' may be different from the extension direction of the leg portion 4. Further, the invention is not limited to the case where the sub-leg portion 4' has the structures of FIGS. 19 and 20. For example, the sub-leg portion may be divided from a certain portion of the leg portion 4 or may extend from the limbus of the lens 2.

Figure 21:
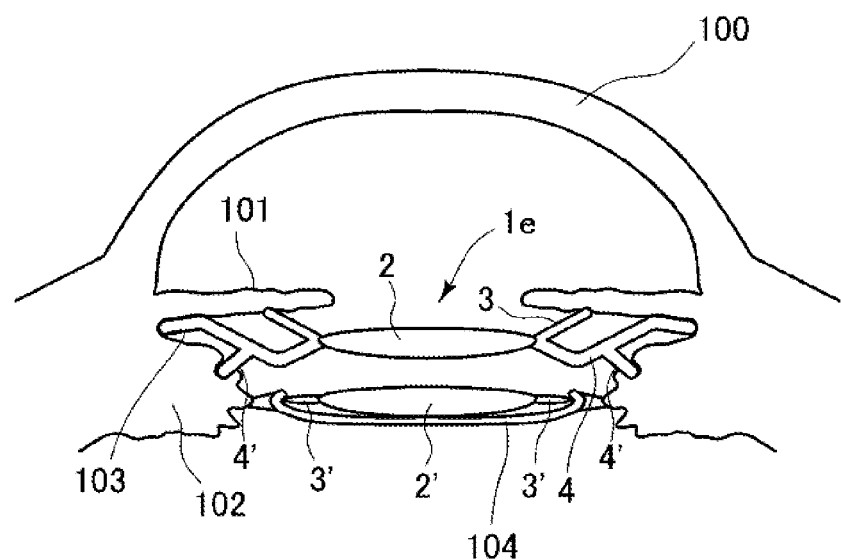
FIG. 21 is a view illustrating a state where an intraocular lens of the seventh embodiment is inserted and fixed into an eye.

An example in which the front lens portion 1e is attached into the eye is illustrated in FIG. 21. As described above, the nipping portion 3 nips a part of the iris, the front end 44 of the leg portion 4 comes into contact with the inside of the ciliary sulcus 103, and the front end of the sub-leg portion 4' comes into contact with the ciliary body 102. As described above, since there is a tendency that the ciliary body 102 is enlarged after the eye lens is extracted, the front end of the sub-leg portion 4' reliably comes into contact with the surface of the ciliary body 102. As a result, the front lens portion 1e is fixed into the eye (the rear section) in a complex manner in which the iris 101 is nipped by the nipping portion 3, the leg portion 4 comes into contact with the inside of the ciliary sulcus 103, and then the sub-leg portion 4' comes into contact with the ciliary body 102.

Figure 22:
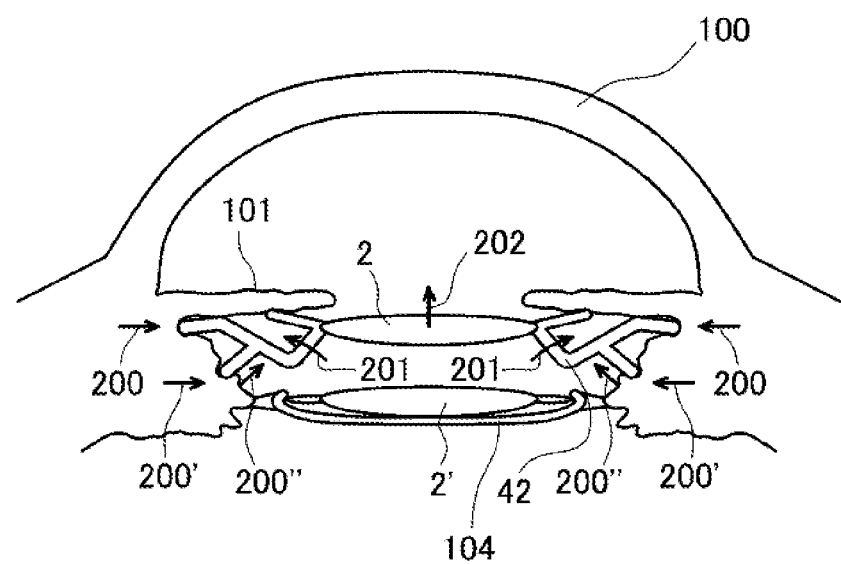
FIG. 22 is a side view illustrating an example of a state where the intraocular lens of the seventh embodiment moves.

The front lens portion 1e further improves the patient's focusing function by forming the sub-leg portion 4'. The shape is illustrated in FIG. 22. According to the knowledge of the inventor, in the case where the patient with the front lens portion 1e attached into the eye wants to focus on an object, a force 200' is also exerted on the ciliary body 102 in addition to the force exerted in the direction of the arrow 200. The force 200' presses the sub-leg portion 4' in the direction of the arrow 200".

Such an action is synthesized with the function in which the force 200 presses the leg portion 4 as described above, the leg portion 4 is twisted, and hence the posture of the root portion 42 of the leg portion 4 is largely changed in the direction of the arrow 201. Accordingly, the lens 2 is largely pressed into the front side inside the eye. When the forces of the arrows 200 and 200' disappear, the lens 2 returns to the original position.

That is, not only the movement of the ciliary sulcus 103, but also the movement of the ciliary body 102 are transmitted to the front lens portion 1e, and hence the lens 2 moves in the front and rear direction. Then, the movement amount of the lens 2 in the front and rear direction may be increased compared to the case where only the movement of the ciliary sulcus 103 is transmitted to the front lens portion. Further, according to the knowledge of the inventor, the expansion and contraction of the ciliary body is relatively larger than that of the ciliary sulcus. Accordingly, the movement amount of the lens 2 in the front and rear direction in the front lens portion 1e increases due to the formation of the sub-leg portion 4'.

When the movement range of the lens 2 in the front and rear direction further increases, the gap between the lens 2 and the lens 2' further increases. Accordingly, the focal distance of the lens system including the lens 2 and the lens 2' further changes. Thus, the patient who wears the front lens portion 1e can focus on an object within a relatively wide distance range from himself or herself.

Figure 23:
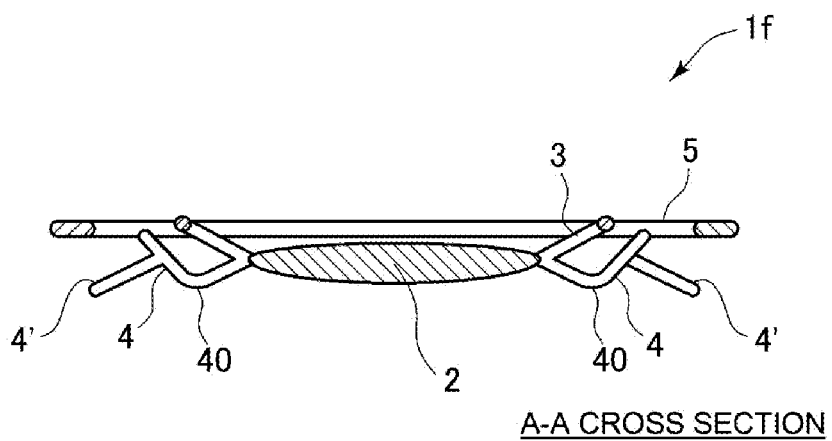
FIG. 23 is a cross-sectional view illustrating a front lens portion of an eighth embodiment.

The structure in which the intraocular lens of the invention comes into contact with the ciliary body 102 is not limited to the above-described example, and any structure in which the intraocular lens comes into contact with the ciliary body 102 may be used. For example, the sub-leg portion 4' may be added to the front lens portion 1a of FIGS. 6 and 7. The eighth embodiment is illustrated in FIG. 23. FIG. 23 is a cross-sectional view taken along line A-A corresponding to FIG. 7 in a front lens portion 1f of an eighth embodiment.

The front view of the front lens portion 1f may be the same as FIG. 6. That is, the extension direction when viewed from the front surface of the sub-leg portion 4' may be the same as the extension direction of the leg portion 4. Alternatively, the extension direction when viewed from the front surface of the sub-leg portion 4' may be different from the extension direction of the leg portion 4. In the front lens portion 1f, as described above, the nipping portion 3 nips a part of the iris, the ring portion 5 comes into contact with the inside of the ciliary sulcus along the circumferential direction, and the front end of the sub-leg portion 4' comes into contact with the ciliary body. With such a complex structure, the intraocular lens is reliably fixed into the eye.

Figure 24:
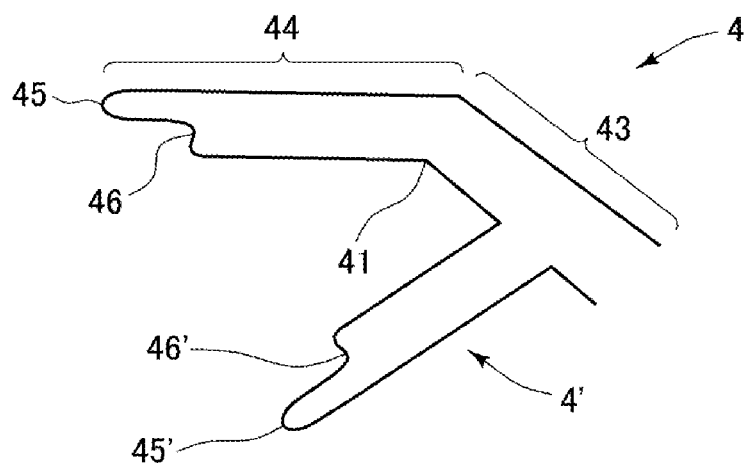
FIG. 24 is a view illustrating an example of a concave portion of a front end of a sub-leg portion.
Figure 25:
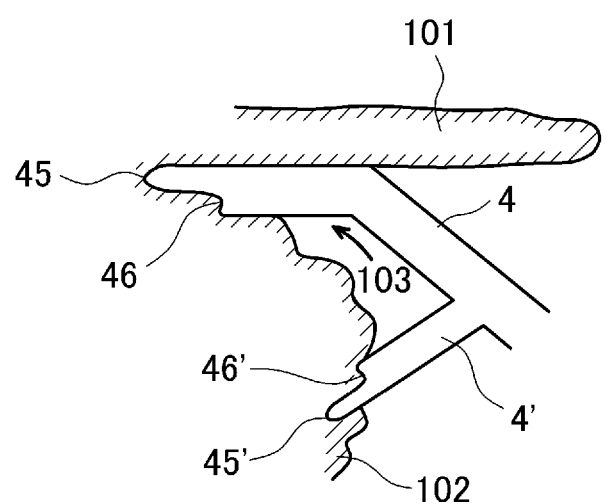
FIG. 25 is a view illustrating the function of the concave portion of the front end of the sub-leg portion.

The concave portion (the convex portion or the uneven portion) formed in the front end of the leg portion 4 illustrated in FIGS. 17 and 18 may be formed in the front end of the sub-leg portion 4'. The example is illustrated in FIGS. 24 and 25. In the example of FIG. 24, a concave portion 46' is formed in the vicinity of a front end 45' of the sub-leg portion 4'. The concave portion 46' may be formed in the front end of the sub-leg portion 4' of each of the front lens portions 1e and 1f.

Accordingly, when the front lens portion is attached into the eye, as illustrated in FIG. 25, the convex portion of the ciliary body 102 is inserted into the concave portion 46' of the sub-leg portion 4', and hence the sub-leg portion 4' is reliably fixed to the surface of the ciliary body 102. The formation target of the concave portion 46' is not limited to the front lens portions 1e and 1f, and the concave portion may be formed in the front end of the contact portion with respect to the ciliary body formed in the front lens portion. Further, the invention is not limited to the case where the single concave portion 46' is formed, but an uneven shape (for example, a plurality of concave portions and a plurality of convex portions) may be formed so as to be fitted to the uneven shape of the surface of the ciliary body 102.

The above-described embodiments of the invention may be appropriately modified without departing from the spirit of claims. For example, the shape and the structure of the nipping portion are not limited to the example of the arm shape, but a shape and a structure may be employed in which at least a part of the rear section side of the iris 101 is nipped and a gap is formed between the lens 2 and the iris 101. Further, the shape of the leg portion 4 is formed so that the leg portion is bent at two positions in the above-described embodiments, but the invention is not limited thereto. For example, a shape may be employed in which the leg portion is bent at more positions (three positions, four positions, or the like). Alternatively, the bending direction may be set to be different from the above-described bending direction. Further, the bent portion may not be bent with a corner, but may be bent in a curve shape (an R-shape).

Further, in the description above, an embodiment has been described in which the nipping portion 3, the extension portion (the leg portion 4 and the ring portion 5), and the sub-extension portion 4' are provided together, but in the invention, only some of the components or only a certain combination thereof may be provided. For example, a configuration may be employed in which the nipping portion 3 is not provided and only the extension portion (the leg portion 4 and the ring portion 5) is provided. Such a shape may be obtained just by removing the nipping portion 3 in FIGS. 1 to 10. Further, the invention may be a structure with three or more lenses by partially including the two lenses in the embodiments described above.

What is claimed is:

1. An intraocular lens comprising:
   a rear lens portion which has a lens function and is adapted to be received in a posterior capsule inside an eye from which an eye lens is extracted while at least the posterior capsule is left; and
   a front lens portion which has a lens function and is adapted to be disposed at the front side inside the eye in relation to the rear lens portion such that the front lens portion is spaced apart from the rear lens portion,
   wherein the front lens portion includes
      a first lens which is adapted to be disposed at a position facing a lens surface of a second lens as a lens of the rear lens portion, and
      a support portion which is adapted to extend from a limbus of the first lens to a position of a part of a region from an iris to a ciliary body inside the eye, supports the first lens, and has flexibility, and
   wherein the support portion includes
      an extension portion which is formed in a shape extending toward a lateral side of the first lens and supports the first lens while a portion farthest from the center of the first lens in the shape is adapted to come into contact with the inside of a ciliary sulcus of the eye, and
      a sub-extension portion which is branched from a side surface of the extension portion, is adapted to extend toward the rear side inside the eye, and is adapted to come into contact with a surface of the ciliary body so that a force of pressing the first lens toward the front side inside the eye is transmitted when the sub-extension portion is pressed by the ciliary body.

2. The intraocular lens according to claim 1,
   wherein one of the first lens and the second lens is a convex lens and the other thereof is a concave lens.

3. The intraocular lens according to claim 1,
   wherein the support portion has a bent shape in which the support portion is adapted to bend in response to the movement of the region from the iris to the ciliary body while a front end of the support portion comes into contact with a position of a part of the region from the iris to the ciliary body inside the eye so that the first lens is movable inside the eye in the front and rear direction.

4. The intraocular lens according to claim 1,
   wherein the support portion includes a nipping portion which is formed in a shape extending toward the lateral side of the first lens disposed at the rear section and is adapted to nip a part of the rear section side of the iris of the eye so as to support the first lens.

5. The intraocular lens according to claim 4,
   wherein the shape of the nipping portion is adapted to be a shape in which a portion nipping the iris in the nipping portion is located at the front side inside the eye in relation to the first lens.

6. The intraocular lens according to claim 1,
   wherein the extension portion has a bent shape, and the bent shape is a shape in which the first lens is movable inside the eye in the front and rear direction in response to the movement of the ciliary sulcus while a portion farthest from the center of the first lens in the extension portion is adapted to come into contact with the inside of the ciliary sulcus of the eye.

7. The intraocular lens according to claim 1,
   wherein the extension portion has flexibility and has a size in which at least a part of the extension portion is bent while a portion farthest from the center of the first lens in the extension portion is adapted to come into contact with the inside of the ciliary sulcus of the eye.

8. The intraocular lens according to claim 1,
   wherein the extension portion includes a plurality of leg portions which are adapted to extend from a plurality of positions of the limbus of the first lens in the circumferential direction in a direction moving away from the center of the first lens due to the leg shape.

9. The intraocular lens according to claim 8,
   wherein a front end of the leg portion is adapted to come into contact with at least a part of a deep portion of the ciliary sulcus while being inserted into the ciliary sulcus of the eye.

10. The intraocular lens according to claim 8,
    wherein the leg portion includes a bent portion which is bent at a position between an end close to the first lens and an end far from the first lens in the leg shape, and
    wherein the leg portion has a shape in which the end close to the first lens in the leg portion is adapted to be located at the front side of the eye in relation to the bent portion and the end far from the first lens in the leg portion is adapted to be located at the front side of the eye in relation to the bent portion so that the first lens is pressed toward the front side inside the eye when the ciliary sulcus presses the leg portion while the first lens is disposed at the rear section of the eye.

11. The intraocular lens according to claim 9,
    wherein the leg portion includes a bent portion which is bent at a position between an end close to the first lens and an end far from the first lens in the leg shape, and
    wherein the leg portion has a shape in which the end close to the first lens in the leg portion is adapted to be located at the front side of the eye in relation to the bent portion and the end far from the first lens in the leg portion is adapted to be located at the front side of the eye in relation to the bent portion so that the first lens is pressed toward the front side inside the eye when the ciliary sulcus presses the leg portion while the first lens is disposed at the rear section of the eye.

12. The intraocular lens according to claim 1,
wherein the extension portion includes an annular ring portion which is inserted into the ciliary sulcus in the circumferential direction.

13. The intraocular lens according to claim 1,
wherein a portion adapted to come into contact with the inside of the ciliary sulcus in the extension portion is provided with a concave portion or a convex portion which is fitted to an uneven portion inside the ciliary sulcus.

14. The intraocular lens according to claim 1, wherein the rear lens portion includes the second lens having a lens function and a loop portion.

15. The intraocular lens according to claim 14, further comprising a pair of loop portions formed at a limbus of the second lens at the opposite side in the optical axis.

* * * * *